United States Patent [19]

Seifert

[11] Patent Number: 5,175,093

[45] Date of Patent: Dec. 29, 1992

[54] BIOACTIVE CELLS IMMOBILIZED IN ALGINATE BEADS CONTAINING VOIDS FORMED WITH POLYETHYLENE GLYCOL

[75] Inventor: Douglas B. Seifert, Whitehall, Pa.

[73] Assignee: Lehigh University, Bethlehem, Pa.

[21] Appl. No.: 433,501

[22] Filed: Nov. 7, 1989

[51] Int. Cl.$^5$ .................... C12P 1/00; C12N 11/10; C12N 5/00; C12N 1/12

[52] U.S. Cl. .................... 435/41; 435/178; 435/240.22; 435/240.23; 435/240.26; 435/240.4; 435/252.1

[58] Field of Search .............. 435/41, 174, 177, 178, 435/182, 240.22, 240,23, 240.26, 240.4, 252.1

[56] References Cited

U.S. PATENT DOCUMENTS

| | | | |
|---|---|---|---|
| 4,352,883 | 10/1982 | Lim | 435/182 X |
| 4,778,749 | 10/1988 | Vasington et al. | 435/2 |
| 4,798,786 | 1/1989 | Tice et al. | 435/177 |
| 4,927,761 | 5/1990 | Reading et al. | 435/178 |
| 4,935,365 | 6/1990 | Nilsson et al. | 435/178 |

OTHER PUBLICATIONS

Familletti and Fredericks, "Techniques For Mammalian Cell Immobilization," Biotechnology, vol. 6, Jan. 1988, pp. 41, 42 and 44.

Pasillico, "Microencapsulation Technology For Large-Scale Antibody Production", Biotechnology, vol. 4, Feb. 1986, pp. 114–117.

Sinacore, "Gel Entrapment:Applications in Production of Biologicals and Mass Culturing of Animal Cells," Karyon Technology, News, vol. 1, No. 2, Sep. 1984.

Geyer, "Optimizing of Culture Systems Utilizing Gel-trap Technology", Karyon Technology News, vol. 2, No. 1, Feb. 1985.

Pobojewski, "New Micro Encapsulation Technique Developed," Genetic Engineering News, Nov./Dec. 1988, pp. 1 and 61.

King, et al., "Alginate-Polylysine Microcapsules of Controlled Membrane Molecular Weight & Cut off for Mammalian Cell Engineering," Biotechnology Progress, vol. 3, No. 4, Dec. 1987, pp. 231–240.

Bucke, "Cell Immobilization in Calcium Alginate," Methods in Enzymology, vol. 135, pp. 175–198.

Nilsson, "Entrapment of Cultured Cells in Agarose Beads," Large Scale Cell Culture Technology, Edited by Bjorn Lyderson, Hanser Publishers, New York, pp. 95–111.

*Primary Examiner*—David M. Naff
*Attorney, Agent, or Firm*—Ratner & Prestia

[57] ABSTRACT

Bioactive cells are immobilized by suspending bioactive cells in an aqueous solution of a salt-free osmolarity adjuster, alginate and polyethylene glycol, dividing the suspension into bead-sized globules, contacting the globules with a solution of divalent cations to gel the alginate to form beads containing polyethylene glycol-filled areas and removing the polyethylene glycol to form voids in the beads entrapping the bioactive cells. By perfusing the beads with a nutrient medium, the cells can proliferate in the voids to produce high cell densities and produce a product which can be separated from the medium.

19 Claims, 4 Drawing Sheets

BIOACTIVE CELLS IMMOBILIZED IN ALGINATE BEADS CONTAINING VOIDS FORMED WITH POLYETHYLENE GLYCOL

BACKGROUND

This invention pertains to an improved form of alginate bead substrate in which bioactive cells, such as mammalian hybridomas, are captured, which substrate is perfusable with nutrient and cell product-carrying media. This invention also pertains to methods for making such a substrate and for using such a substrate, particularly to produce and to harvest cellular products in a continuous manner.

Gelled alginate beads are known to be useful as immobilization substrates for bioactive cells of various types, including bacteria, yeast, plant cells, hybridomas and animal tissue, for culturing such cells and for harvesting products thereof. This technology, with specific references to animal cells, is disclosed generally, for example, by C. Bucke (Cell Immobilization in Calcium Alginate, Methods in Enzymology, Vol. 135, pp. 175-189 (Academic Press, Inc. 1989)) and G. A. King et al., (Alginate-Polylysine Microcapsules of Controlled Membrane Molecular Weight Cutoff for Mammalian Cell Culture Engineering (Biotechnology Progress, Vol 3, No. 4, Dec. 1987, pp. 231-240)). A discussion of the specific application of such immobilization technology to the capture and culturing of animal cells has also been described by K. Nilsson (Entrapment of Cultured Cells in Agarose Beads, Large-Scale Cell Culture Technology, pp. 96-111 (Hanser Publishers, Distributed by MacMillan Publishing Company)).

Specific processes and materials for immobilizing and using animal cells in alginate gel beads has been the subject of research by the Hoffmann-LaRoche Company, of Nutley, N.J. 07110, Damon Biotech of Needham Heights, Mass. 02194, Karyon Technology, Inc. (subsequently acquired by the Schering Plough Company) and the University of Michigan, which research is believed to be reflected respectively in the following publications:
1. Techniques for Mammalian Cell Immobilization, Familletti and Fredericks, Bio/Technology, Vol. 6, January 1988, pp. 41-44.
2. Microencapsulation Technology for Large-Scale Antibody Production, Posillico, Bio/Technology, Vol. 4, February 1986, pp. 114-117.
3a. Karyon Technology News, September 1984;
3b. Karyon Technology News, February 1985;
3c. U.S. Pat. No. 4,778,749—Frye et al.
4. New Macroencapsulation Technique Developed, Pobojewski, Genetic Engineering News, November/December 1988, pp. 1 and 61.

As indicated in the September 1984, Karyon Technology News, supra, animal cell growth occurs when cells are entrapped in alginate beads which are then placed in a standard tissue culture media. Cell proliferation is made possible as a result "of the high porosity of the beads allowing for diffusion of nutrients and waste products into and out of the gel matrix." U.S. Pat. No. 4,778,749 also indicates that the porosity of the alginate gel beads, in which the cellular material is immobilized, is important, but does not indicate the extent of this porosity or how it is produced.

In the Damon Biotech procedure (reference 2 above), cells are encapsulated in a two-stage process. Cells are first immobilized in a gelled sodium alginate sphere. These spheres are then coated with a biopolymer, more specifically, a semi-permeable membrane layered onto the periphery of the gelled sphere by step-wise addition of reagents including a polycationic polyamino acid compound that binds to the alginate (polyanion) spheres through salt-bond formation. When the capsule is complete, brief exposure to a chelating agent reliquifies the intracapsular alginate, allowing cells to migrate within the capsule and facilitating diffusion of nutrient medium into the capsules. Cells are protected within the capsules, and large biomolecules, (greater than 60,000 molecular weight) secreted by cells trapped in the capsular space, are trapped until harvesting.

In the University of Michigan process (reference 4 above), cells to be cultivated are mixed in a dilute calcium chloride solution which is then added dropwise to an alginate solution and forms capsules. The gelled alginate is said to remain on the outside of the capsule while calcium fuses to the surface and forms a thin skin, enabling researchers to tailor the capsule to a given thickness and size with specific characteristics.

The Hoffmann-LaRoche approach (see reference 1 above) is to combine alginate with solid gelatin particles and then to gel the Alginate as beads. By heating the beads to 37° C., at which temperature the gelatin liquifies, cavities are formed in the alginate matrix. Upon culturing, cells originally disposed in the alginate suspension grow into the void space created by liquification of the gelatin.

Bead size in this procedure is said to be 8 mm in diameter. Similar work by the present inventor confirms that, because of the large solid particle size of gelatin, this method cannot be used for the production of small beads. Large particle size alginate beads exhibit relatively poor mass transport of nutrients and cellular products to the cells in the core of the bead.

Notwithstanding the foregoing background work and efforts of others, there remains a need for an improved substrate capable of immobilizing bioactive cells, such as mammalian cells on the order of 15 $\mu$ in diameter, which substrate permits ready accessibility to the immobilized cells, of nutrient and/or cellular product-carrying media.

BRIEF DESCRIPTION OF THE INVENTION

Polyethylene glycol (PEG), having a molecular weight of about 200 to 10,000, preferably about 8000, is dissolved in an alginate solution (preferably buffered to about neutral pH). The weight per cent concentration of PEG is between 10 wt % and 30 wt %, and that of alginate, between 0.25 wt % and 5 wt %. Preferably, bioactive cells, such as mammalian cells, insect cells and particularly mammalian hybridomas, having maximum produced, and minimum cell dimensions of about $\frac{1}{2}$ $\mu$, but preferably of a size between 10 $\mu$ and 30 $\mu$, are then suspended in the alginate-PEG solution. Relatively small sub-divided portions (droplets) of the suspension (between 20 $\mu$ and 5 mm, preferably 0.5 mm to 5 mm) are contacted with a divalent cation-containing solution, such as by immersing such sub-divided portions in a calcium chloride bath, to gel the alginate and thus to form alginate beads.

The beads thus produced range from 20 $\mu$ to 5 mm, (preferably 0.5 mm to 5 mm ) in maximum particle size dimension. The beads shrink slightly (about 10 %) when gelled. The upper limit of the size of the alginate gel beads is essentially limited by the ability to provide suitable nutrients to sustain viability of the cells in the bead. This depends upon a number of factors including the size of a bead, the alginate density, and the concentration of cells per bead.

The beads as initially produced, are composed of a PEG phase dispersed as a multiplicity or network of shaped or discrete sub-divisions or inclusions within and enclosed by a gelled alginate matrix phase. The PEG is subsequently extracted by washing the alginate beads, such as with isotonic saline (8 g/liter), leaving an alginate matrix surrounding a multiplicity of discrete void spaces. The bioactive cells from the alginate/PEG/cell suspension remain disposed in or near these void spaces (or macropores), enclosed within the alginate matrix of each bead.

In use, such beads, enclosed within a reactor for example, may be perfused with a media which readily diffuses through the internal structure of the beads, to provide nutrients to the cells immobilized therein and/or to remove cellular products, such as secretions, enzymes, antibodies, etc. therefrom. Moreover, this process may be conducted in a continuous, as contrasted to batch, mode, enabling the user to produce and to harvest such cellular products continuously over an indefinite period of time.

DETAILED DESCRIPTION OF THE INVENTION

Figure 1:
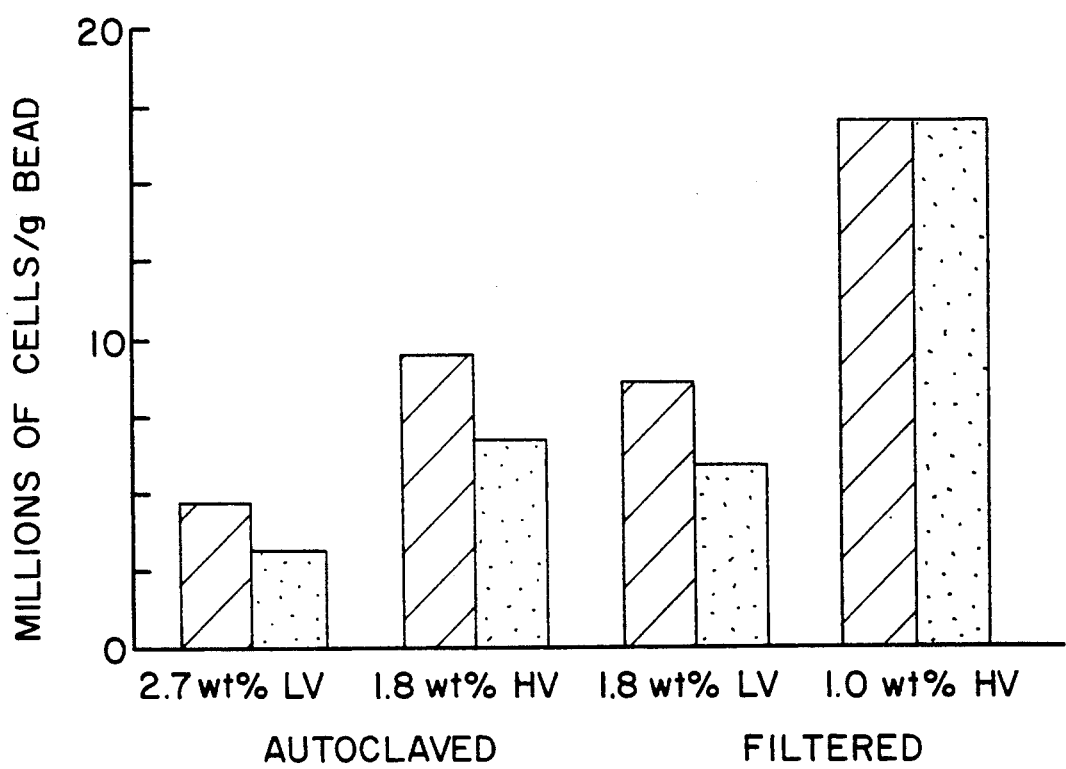
FIG. 1 is a graph showing the effect of the alginate concentration on the maximum cell density achieved in alginate beads without PEG.

It has now been discovered that bioactive cells, either alone in suspension or, in the case of anchorage-dependent cells, attached to dimensionally compatible anchorage sites, can be immobilized for culturing and/or for harvesting of cellular products, by entrapping the cells or cell-anchorage site combinations, in macropores of a gelled alginate bead matrix. Anchorage dependent cells are those cells that, when presented with the appropriate chemical anchorage cite, will chemically bond to the anchorage site, yet continue to live and grow.

"Bioactive" cells useful herein include any cell which grows and/or reproduces and/or produces a cellular product. Typically this includes, at the lower end, cells on the order of the size of bacteria (about $\frac{1}{2}$ $\mu$) up to and including insect cells and mammalian cells (including mammalian hybridomas), which are typically in the 10 $\mu$ to 25 $\mu$ range. At the upper end, the size range of bioactive cells is limited only by the size limitation, if any, of the beads in which the cells are entrapped. Due to the fact that alginate gel is, to some degree, porous, even aside from the macropores formed by the PEG, cells below $\frac{1}{2}$ $\mu$ will tend to leak through the porous gel. For that reason, the beads will hold larger cells better. Therefore, cells larger than 10 $\mu$ are preferred. Cells below 30 $\mu$ are also preferred because larger cells require larger beads for entrapment and such larger beads are more limited in diffusability (or perfusability) of carrier media.

An important use of the alginate-bead entrapped bioactive cell product of this invention is the continuous production of cell (or cellular) product. For this purpose, the beads are housed in a reactor and a liquid medium is perfused through the beads, as it is continuously introduced into and withdrawn from the reactor. Nutrients, for cell growth and continued viability, may be carried by this medium into the alginate bead matrix and into contact with the cells entrapped there. Cellular product may also be removed by the medium from the cells and the beads. Any tissue culture medium, suitable for use with the cells to be cultivated, may be used. Many such tissue culture media are available from Sigma Chemicals of St. Louis, MO. The medium chosen should not be high (above 5 mM) in phosphate. Phosphate is a chelating agent, and as previously discussed (in the background relating to the Damon Biotech procedure), chelating agents tend to dissolve alginate beads. Further, the medium must be capable of mass transport of nutrients and cellular products to and from the cells in the beads. The media must not damage the cells or beads. The particular medium chosen will depend on the particular cells used, and what is desired to be done with the cells, e.g. multiplication of cells, harvesting of cells, cellular product recovery, etc. One such medium which may be used for this purpose (for multiplication and cellular product recovery of HB 121 hybridomas) is Dulbecco's Modified Eagle Medium (DMEM) available from Sigma Chemicals.

In one method of use embodiment, nutrient for growth and reproduction would be supplied only until optimum cell population had been reached. After that, nutrient (including for example, an oxygen supply, if necessary) would be supplied only to the extent required for continued viability. For that purpose, and for harvesting of cell product, perfusion would be continued indefinitely. One advantage of this process is that the cellular product may be produced and harvested continuously and the harvested product may be essentially cell-free.

If harvesting of the cell culture is the objective, of course, the process would be operated in batch mode and the alginate gel matrix liquified (preferably by introduction of a chelating agent) at the conclusion of the process.

Cell immobilization beads of this invention comprise an alginate matrix formed by contacting small sub-divisions or droplets of a dilute alkali metal alginate/polyethylene glycol solution, normally also including bioactive cells in suspension, with a divalent ion-containing solution, such as a calcium chloride solution, which causes the alginate to gel as beads. Alginate will form beads with almost any polyvalent ion, and divalent ions such as $Ca^{2+}$, $Sr^{2+}$, and $Ba^{2+}$ are commonly used. Several types of alginate are available for cell immobilization. *Cell immobilization in Calcium Alginate*—Bucke, supra, describes such a process (without polyethylene glycol) for making alginate beads with cells immobilized therein. Table One thereof, p. 178, shows several different types of alginate available. Alginate is generally available as an alkali metal salt of alginic acid, such as sodium alginate.

When the alginate contacts a solution containing a divalent ion, such as calcium, the alginate immediately forms a three-dimensional polymeric matrix. Thus, beads of alginate matrix are formed by adding alginate drop-wise to a calcium solution. The beads thus formed are nearly spherical in shape when the viscosity of the alginate is 200–500 cp., corresponding to the shape of the alginate droplet. A minimum viscosity must be maintained or the droplets will deform upon contact with the surface of the calcium chloride solution. FIGS. 2-5 show beads formed by the method of this invention, using an alginate/cell mixture, with varying amounts of PEG.

Bioactive cells to be immobilized are included in the alginate/polyethylene glycol solution. Thus, when the bead forms, the cells are trapped in the alginate matrix. It is important that the beads formed be small enough to permit good mass transport of culture medium into and out of the beads in order to feed the cells and carry cell wastes and product away from the cells through the matrix.

The calcium chloride ($CaCl_2$) solution should contain a buffer if necessary for the cells. In the case of mammalian cells, HEPES (N-2-Hydroxyethylpiperazine-N-2-ethanesulfonic acid) is a useful buffer to maintain a pH acceptable to the cells which, in the case of mammalian cells, is essentially neutral (pH 7.4). The proper pH (and the proper buffer) will depend upon the particular cell line used. In some cases, such as bacteria, the cells can tolerate a wide range of pH, and it may not be necessary to use a buffer.

In one embodiment of the present invention, the alginate/PEG/cell solution is extruded through a hypodermic syringe, preferably equipped with a 22G needle, while a stream of air flows concentrically around the needle. As the drops of solution/suspension are formed on the needle, the air flow causes the drops to break off into bead-sized globules, and the sub-divisions of solution/suspension thus formed drop a few centimeters into a $CaCl_2$ solution. The droplet, and thus the bead, size may be controlled by controlling the air flow rate.

Alternatively, in order to decrease the diameter of the beads, which correspond to the size of the drops from which they are formed, the size of the drops may be decreased in another way. A resonance vibration may be set up in the extruder (hypodermic syringe) by connecting a vibrator to the silicone tubing which delivers the solution to the syringe. By adjusting the frequency of the vibrator, a steady stream of small droplets may be extruded. Bead sizes as low as 20 $\mu$ have been achieved with these methods.

By way of background, it should be understood that, in a continuous reactor, productivity will depend on, on among other things, both bead density (in the reactor) and cell density (in the beads). For good production rates, it is desirable that the concentration of cells in the reactor be as high as possible, and preferably at least $1 \times 10^7$ viable cells/ml reactor volume. Since the reactor volume is generally a minimum of 10% beads, the cell density of the beads should be at least $1 \times 10^8$ cells/ml bead. Even so, it is preferable to use a bead loading of 20% in the reactor. Thus, if the cell density in the bead is $10^8$ cells/ml bead, the resultant cell density in the reactor should be $2 \times 10^7$ cells/ml reactor volume.

To achieve such high cell densities, it is desirable to reduce the alginate matrix density in the bead in order to allow additional room for cells. FIG. 1 shows the cell density in cells/g bead in beads made from alginate of differing concentrations. Keltone LV has a lower molecular weight than Keltone HV, so a higher concentration of Keltone LV is needed to form a solution of sufficient viscosity to form beads.

Autoclaving reduces molecular weight and therefore the viscosity of the alginate, requiring even greater concentrations of alginate, and therefore sterile filtering is the preferred method of sterilization. FIG. 1 shows, with two trials for each alginate, even at the lowest alginate concentration possible, while still maintaining the proper viscosity, using alginate without PEG cell density approached only $2 \times 10^7$ cells/ml bead, and was lower for lower molecular weight alginates. Note that these trials were performed with alginate, not including PEG as in the present invention. These factors are also applicable, however, and should be taken into account in using the present invention.

As also demonstrated with alginate not including PEG, maintaining a sufficient viscosity to prevent break up of the alginate droplets on the surface of the calcium chloride solution, while decreasing the concentration of the alginate in the mixture, is difficult. For that purpose, a very high-molecular weight alginate was selected, (Keltone HV, available from Kelco, a division of Merck & Co., Clark, N.J.) and combined with various possible viscosity modifiers. Surprisingly, polyethylene glycol (PEG, molecular weight 8000) was found to increase the viscosity of the solution at low concentrations of alginate, and was found to yield other very highly desirable results, namely discrete, generally symmetrical inclusions in the alginate beads. It was found that these inclusions contained PEG, and that the PEG will diffuse out of the beads, resulting in the highly advantageous macroporous beads of the present invention.

Even apart from its utility in forming the macropores in the bead product of this invention, PEG is also especially useful as a viscosity modifier because of what is known as the viscosity bonus effect. The viscosity bonus effect is a multiplicative increase in the viscosity of a polymer solution placed in modified solvent system. The effect can be described by the following example. Adding glycerol to distilled water may increase the viscosity from 1 centipoise (cp) to 2 cp. If a carboxymethyl-cellulose (CMC) solution which is normally 100 cp in distilled water is prepared in the glycerol/water system, the viscosity increases to 200 cp.

Therefore, the viscosity bonus effect phenomenon was studied in order to facilitate significant reductions in alginate concentration. Specifically, glycerol was tested since such a low molecular weight solvent as glycerol would quickly diffuse out of the beads, eliminating the possibility of long-term toxicity problems.

Indeed an alginate/glycerol system was initially attempted, and found to produce good beads with high porosity (but not macropores as in the present invention) and low alginate density. However, mammalian cells can not survive in such a system, due to the very high osmolarity (2930 mOs/kg as compared to 308 mOs/kg for physiological saline) of the alginate/glycerol/cell system. Therefore, glycerol proved unacceptable.

In contrast, polyethylene glycol (osmolarity at 20 wt %, 321 mOs/kg. close to the osmolarity of physiological saline) does effectively increase the viscosity of the alginate/cell system to an acceptable level, while also producing the other desirable features described herein, including a highly compatible environment for viability of and diffusivity through mammalian cells immobilized therein. For other types of bioactive cells, the osmolarity may need to be adjusted. This can be accomplished by adjusting either the wt % of PEG in the starting alginate/cell/PEG mixture, or by adding an osmoticum to adjust the osmolarity to an acceptable value.

Initially, it was found that alginate was not soluble in 20 wt % PEG dissolved in saline. Saline is the previously accepted solvent for preparation of gelled alginate/cell beads. Accordingly, the alginate/PEG solution used in the present invention must be prepared with distilled water. One such useful solution is a 0.5 wt % Keltone HV/20 wt % PEG 8000 in distilled water. This solution has a viscosity of 310 cp which is acceptable for bead formation.

In one set of experiments it was found that the bead-forming mixture in the present invention should contain between 0.25 and 5 wt % alginate, and 10–30 wt % PEG. Keltone HV is preferred for use with the present invention, however other alginates commonly used for bead production may also be used. Alginates with high molecular weight, and more particularly high viscosity are preferred. The remainder of the PEG/alginate mixture should be milli-Q water or equivalent. Before addition of cells to this PEG/alginate mixture, the mixture should be sterile filtered (as opposed to autoclaved for reasons indicated above). The mixture may also be autoclaved, however, this reduces the molecular weight and viscosity of the alginate, which necessitates the use of higher concentrations of the alginate in the PEG/alginate mixture in order to achieve an acceptable viscosity.

The PEG/alginate mixture is then mixed with the desired cell inoculum. Within the size range indicated above, any cells should be immobilizable, including the full range of bacteria to plant cells. It should be kept in mind, however, that smaller cells cause higher cell leakage rates, while larger cells may necessitate greater bead size, causing diffusion problems in getting nutrients to the center of the bead. Therefore, as indicated above, cells between 10 $\mu$ and 30 $\mu$ are preferred for use in this invention. It is thought that cells smaller than $\frac{1}{2}$ $\mu$ will tend to leak through and be lost from the alginate matrix. Cells larger than 30 $\mu$ such as plant aggregates may be too large for effective encapsulation in a bead which will be readily perfusable with a nutrient and/or product carrying medium.

The cells used in the examples which follow were HB 121 cells, which have a size (maximum dimension) of about 15 $\mu$.

EXAMPLES

The PEG/alginate/cell mixture was made by combining 3 parts of the PEG/alginate mixture with one part isotonic 9 wt % sucrose solution containing between 4–8×10$^6$ viable cells/ml. Thus the PEG/alginate/cell mixture contained about 1–2×10$^6$ viable cells/ml.

Beads, with immobilized cells, made from this PEG/alginate/cell mixture are most notably characterized by generally symmetrical networks, comprised of a multiplicity of voids or enclosed spaces. It is thought that because of this macroporosity, the beads of this invention comprise a substrate for immobilized cells, which supports a higher concentration of cells per bead than would otherwise be achievable with a solid alginate matrix and which is much more readily diffusible, providing more effective perfusion through better access of perfusion medium to cells in the essentially free space of the macropores in the matrix structure of the beads.

Figure 2:
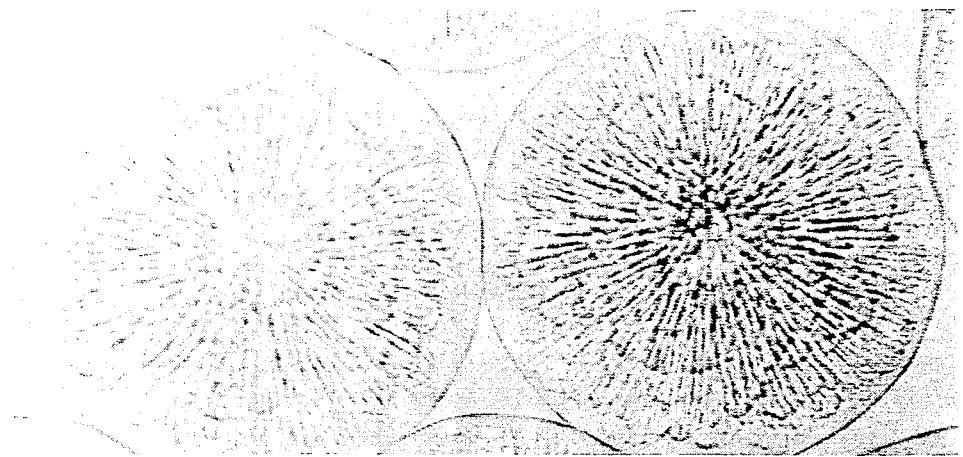
FIG. 2 is a photo-micrograph of the beads of the present invention prepared with 20 wt % PEG 8000.
Figure 3:
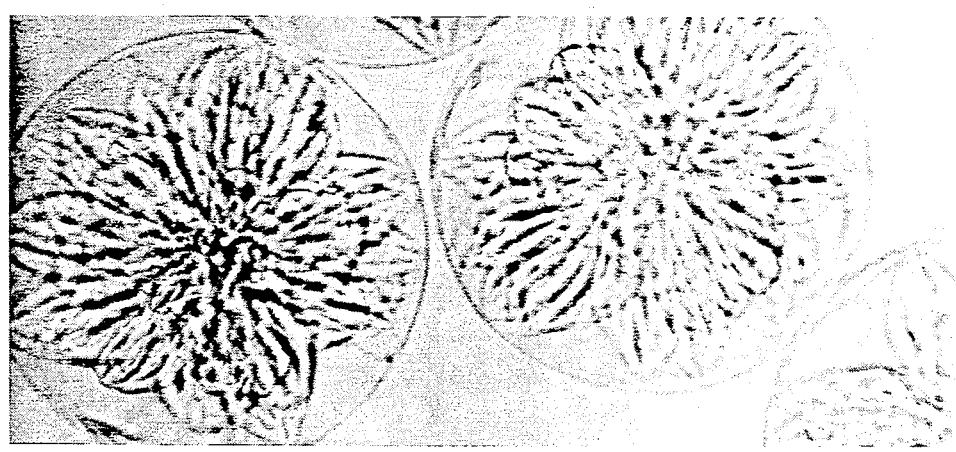
FIG. 3 is a photo-micrograph of the beads of the present invention prepared with 15 wt % PEG 8000.
Figure 4:
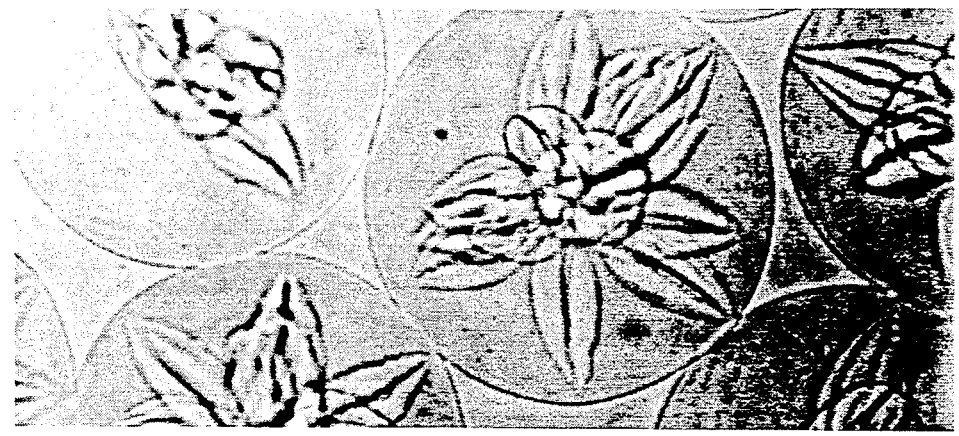
FIG. 4 is a photo-micrograph of the beads of the present invention prepared with 10 wt % PEG 8000.

The following examples were performed to determine the effect of PEG 8000 (polyethylene glycol with a molecular weight around 8000) concentration on the macroporous network in resulting alginate beads. Beads of a diameter of 0.8 mm were formed by the vibration technique (described above) using 0, 10, 15, and 20 wt % PEG 8000 with Keltone HV in the following proportions: 10 wt % PEG 8000/0.75 wt % Keltone HV; 15 wt % PEG 8000/0.75 wt % Keltone HV; 20 wt % PEG 8000/0.75 wt % Keltone HV; 0 wt % PEG 8000/1 wt % Keltone HV. The variations in bead internal structure can be seen in FIGS. 2–4 which are photomicrographs of the beads of the present invention, taken at 40X magnification. FIG. 2 shows 20 wt % PEG, FIG. 3 shows 15 wt % PEG, and FIG. 4 shows 10 wt % PEG, all with 0.75 wt % Keltone HV. As the PEG concentration increased, the pores decreased in diameter and increased in number. It can be readily appreciated therefore, that the pore diameter can be optimized for growth of various cell lines by altering the PEG concentration. In general, as illustrated in FIGS. 2–4, the macropores in the bead substrate of this invention, allow increased cell densities in the alginate beads through lower bead density and higher porosity.

Figure 5:
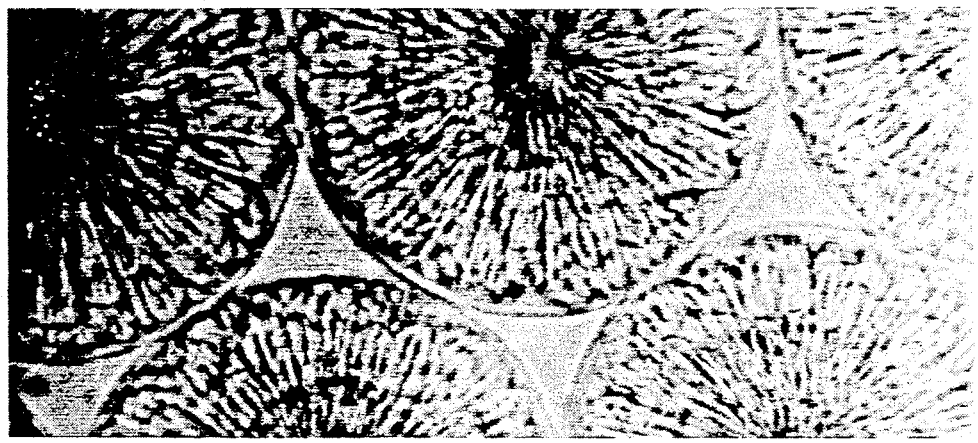
FIG. 5 is a photo-micrograph of the beads of the present invention prepared with 20 wt % PEG 8000 in an isotonic sucrose (9 wt %) solution.
Figure 6:
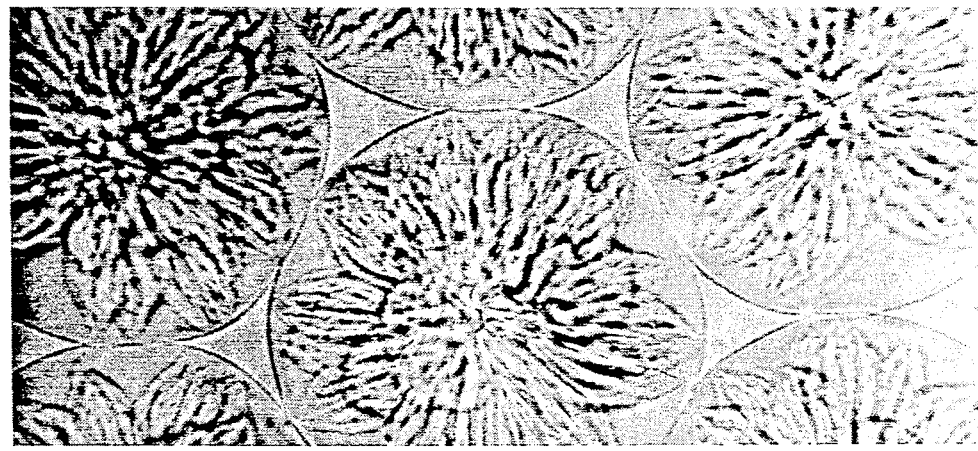
FIG. 6 is a photo-micrograph of the beads of the present invention prepared with 15 wt % PEG 8000 in an isotonic sucrose (9 Wt %) solution.
Figure 7:
FIG. 7 is a photo-micrograph of the beads of the present invention prepared with 10 wt % PEG 8000 in an isotonic sucrose (9 wt %) solution.

However, in a PEG system of the present invention, a high concentration of saline (such as 8 g/liter, isotonic saline) causes precipitation of the alginate. Low concentrations (2 g NaCl/liter) of saline causes the macropores in the product of this invention, to increase in size and decrease in number. This is undesirable. Therefore, an isotonic (9 wt %) sucrose solution (approximately 300 mOs/kg) was used for the cell suspension instead of NaCl. Since the osmolarity of a 20 wt % PEG 8000 system is in the physiological range for mammalian cells, little or no adjustment should be required. Sucrose ca be added to adjust the osmolarity of the alginate/PEG solution when a lower PEG concentration is used. As shown by FIGS. 5 thru 7, sucrose has no effect on the network of macro pores formed in the PEG/alginate/cell system. FIGS. 5 thru 7 are photo-micrographs, taken at 40× magnification, of the beads of the present invention prepared in an isotonic sucrose solution.

A further experiment was performed to determine whether cell growth within the beads would be constrained by the alginate matrix, as was a problem with previous solid alginate matrix beads. Beads were prepared according to the method of the present invention using HB 121 mammalian hybridoma, and compared with identical cells in suspension medium. Both were allowed to grow over an eight day period. At the end of eight days, the maximum cell density of the beads was 5×10$^7$ viable cells/g bead. This corresponds to 2×10$^6$ viable cells/ml culture medium, which is the same as the concentration of cells that the suspension culture reached. This indicates that the cells are not limited by the spacial constraints of the matrix. Further, cell leakage in the PEG/alginate system was negligible. This is much better than conventional alginate immobilized cells, which consistently allow leakage.

A PREFERRED EMBODIMENT AND FURTHER DESCRIPTION

Following is a detailed description of a preferred embodiment of the procedure of the present invention:
1. Prepare a PEG/alginate solution of 0.933 wt % Keltone HV, 18.67 wt % PEG 8000, and 2.25 wt % sucrose in Milli-Q water, and filter sterilize the solution.
2. Prepare 9 wt % sucrose solution with 2mM pH 7.4 HEPES buffer.
3. Prepare a Dulbecco's phosphate buffered saline solution, replacing the phosphate with 10 mM pH 7.4 HEPES buffer.
4. Prepare a 100mM $CaCl_2$ solution in 10 mM pH 7.4 HEPES buffer and sterilize the $CaCl_2$, saline, and sucrose solutions.
5. Prepare a cell inoculum by harvesting a late exponential phase culture, washing once with pH 7.4 saline, once in 9 wt % pH 7.4 sucrose, and resuspending $8 \times 10^6$ viable cells/ml in 9 wt % pH 7.4 sucrose.
6. Mix 3 parts of the PEG/alginate system with 1 part cell suspension.
7. Immobilize the cells by adding the PEG/alginate/cell mixture to the $CaCl_2$ solution dropwise using either the vibration or air jet technique.
8. Remove the $CaCl_2$ solution and wash the beads twice in saline. Allow 15 minutes between each wash so that the PEG 8000 can diffuse out of the beads.
9. Resuspend the beads in culture medium such as DMEM.

It is not possible to achieve high cell densities in normal alginate matrices due to spatial constraints of the matrix. Since the average pore size of a conventional alginate bead is about 15 nm, and the average hybridoma cell diameter is about 15 $\mu$, the cells can proliferate by either breaking down the calcium alginate network or growing in voids in the matrix structure. Since the mammalian cell membrane is fragile, it is not likely that sufficient pressure could be exerted by the cells to break the alginate matrix. Consequently, it is thought that when the cells are immobilized in a conventional alginate, only the cells that become entrapped near a void can proliferate. Furthermore, the extent of the proliferation is limited by the size of the void.

The PEG 8000/water system is a non-toxic, isotonic solvent system that allows a 25% to 50% reduction in alginate concentration with good bead formation. This provides not only a porous matrix for high cell density growth, but also the macropores described earlier. The environment for dense growth in the network of macropores projecting radially from the bead center in the present invention is thought also to be superior to that provided in the large cell clumps which develop in the single large enclosed space occurring in hollow beads such as those formed, for example, by the Damon Biotech procedure discussed previously. This is believed to be caused by more effective diffusion of nutrient medium through the matrix and enclosed spaces in the present invention, as opposed to that through the clumped cell mass in the hollow bead substrates of the prior art. More specifically, the development of cell density in any given mass is limited by the ability to get nutrients into, and wastes and products out of, the center of the mass. This is not possible if the mass becomes too large, resulting in dead cells in the mass center.

Figure 8:
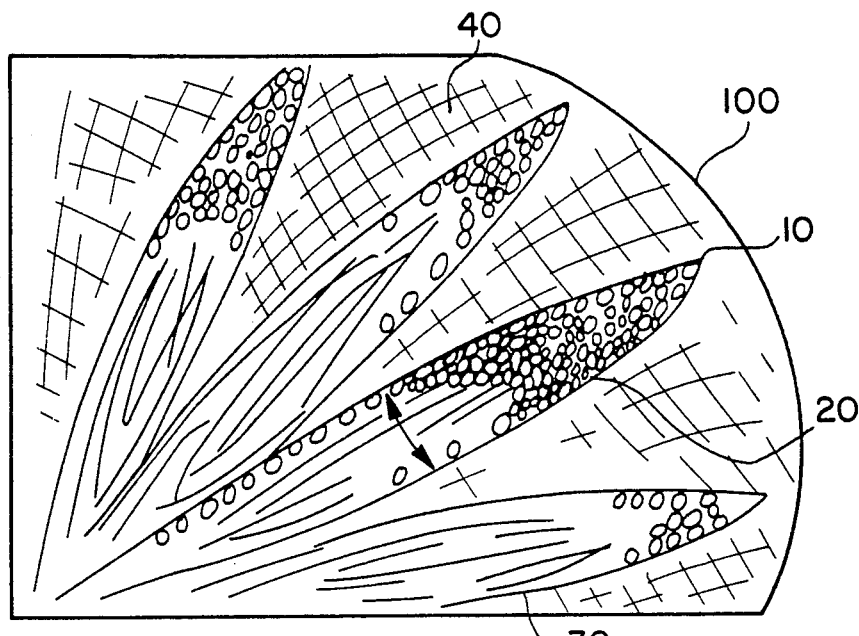
FIG. 8 is a schematic cross sectional view of a part of a bead of the present invention.

As FIG. 8 illustrates, in bead 100 of the present invention, the growth of cell layers 20 (composed of cells 10) is limited by the diameters of macropores 30. Thus nutrients may more readily diffuse through alginate matrix 40 to the effectively greater surface area of the growing cell masses in those macropores. This is preferable to either a solid matrix with small void imperfections, or a shell with no rigid internal matrix structure.

EXAMPLE OF CONTINUOUS PROCESS

A sample perfusion run was performed as described below:
1. A PEG/alginate mixture was prepared by mixing;
   a) 18.66 g Keltone HV in 981.34 g Milli-Q water, and
   b) 346.6 g PEG 8000 and 73.2 g sucrose in 580.2 g Milli-Q water, in equal parts, and filter sterilizing;
2. A cell culture medium was prepared by starting with enough dry DMEM for 10 liters; adding enough Milli-Q water to make up 10 liters; and adjusting the pH to 7.4 with 1 M HCl;
3. 1000 ml horse serum and 111 ml fetal bovine serum were added to the cell culture medium;
4. Five liters of a calcium chloride solution containing 100 mM $CaCl_2$, 5 mM pH 7.4 HEPES buffer, and 0.001% Pluronic L61 (a surfactant available from BASF-Wyandotte) was prepared;
5. Two liters of a sucrose solution containing 9 wt % sucrose and 2 mM pH 7.4 HEPES buffer was prepared;
6. Seven liters of a saline solution containing 0.4 g/liter KCl, 0.1 g/liter $MgCl_2 \cdot H_2O$, 8.0 g/liter NaCl, and 1.3 g/liter (5 mM) pH 7.4 HEPES was prepared;
7. Hybridoma HB 121 cells in late exponential phase were harvested from roller bottles by centrifugation at $150 \times g$ for 6 minutes, resulting in $2.2 \times 10^9$ viable cells;
8. The cells were washed with 100 ml sucrose solution, resuspended in sucrose solution with a total volume of 230 ml, and 225 ml was mixed with 675 ml of alginate solution, resulting in 900 ml alginate/PEG/cell suspension with a cell density of $2.4 \times 10^6$ viable cells/ml;
9. One half liter of alginate/PEG/cell suspension was formed into beads by dropwise addition to the calcium chloride solution, and the beads were allowed to cure for 30 minutes;
10. The calcium chloride solution was replaced with the saline solution and the beads were allowed to stand for 15 minutes, this step was performed twice;
11. The saline solution was replaced with the cell culture medium;
12. The beads were kept at 37° C., with 25% air saturation and pH 7.3, and agitated at 50 rpm; after 15 hours, fresh medium was introduced at 10 ml/$10^9$ viable cells/hr.

Figure 9:
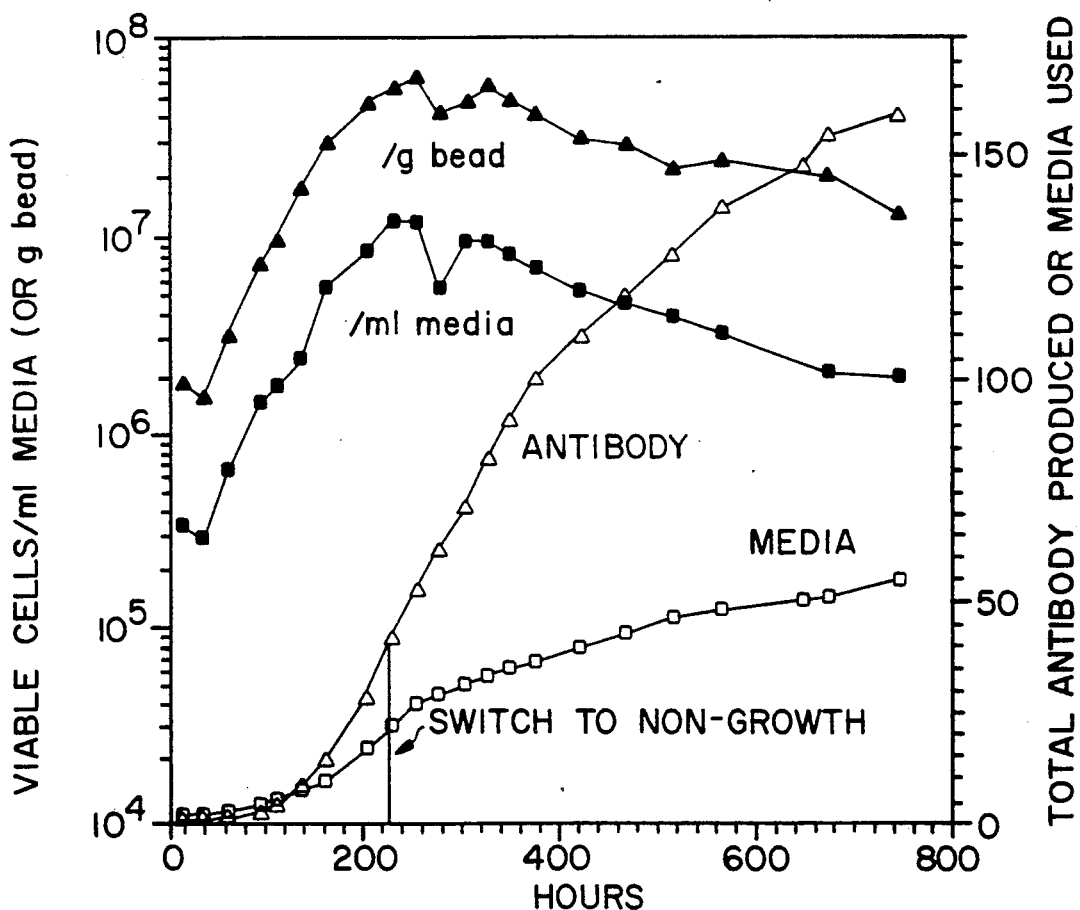
FIG. 9 is a graph showing cell growth, antibody production, and medium consumption in a continuous process of the present invention.

The performance of the perfusion reactor over about 780 hours of operation is depicted in FIG. 9. The culture was operated in a growth phase as well as a non-proliferative production phase. The culture was initiated at $3.4 \times 10^5$ viable cells/ml reactor volume ($1.8 \times 10^6$ viable cells/g bead). The culture increased exponentially with an average growth rate of 0.02 hr At 230 hours, the culture reached a density of $1.2 \times 10^7$ viable cells/ml reactor volume ($6.4 \times 10^7$ viable cells/- bead). A hole in the aerator prevented the use of higher aeration rates, so the growth phase was terminated by switching to a non-growth medium containing 0.1 v/v % serum. After one day (to aid in washing out the reactor) the flow rate of medium was halved.

Antibody accumulation continued throughout the experiment, which was terminated after 30 days. The results of this experiment can be seen in FIG. 9. Culture viability at the end of the experiment was 20%. Optimizing the conditions of the non-proliferative state so that a higher viability is maintained should increase the production of antibody. The results of the continuous perfusion experiment were compared with results of cultures maintained in batch suspension in a reactor and in roller bottles, and in a batch immobilized in alginate/PEG beads and cultivated in roller bottles. The results are given in Table 1.

TABLE 1

| Cultivation Method | Titer ml reactor vol/hr | Titer ml media used/hr | Cultivation Time (hours) | Total Media Used (liters) | Total Titer |
|---|---|---|---|---|---|
| Batch (Reactor) Suspension | 3.3 | 3.3 | 175 | 1.88 | $1.1 \times 10^6$ |
| Batch (RB)* Suspension | 4.4 | 4.4 | 275 | 0.15 | $1.8 \times 10^5$ |
| Batch (RB)* Immobilized | 4.4 | 4.4 | 274 | 0.15 | $1.8 \times 10^5$ |
| Perfusion Growth Phase | 48.8 | 4.3 | 230 | 21.30 | $2.1 \times 10^7$ |
| Perfusion Non-Growth Phase | 59.8 | 3.3 | 516 | 33.60 | $5.8 \times 10^7$ |

*RB refers to the use of roller bottles for the culture

Table 1 shows that the specific antibody rate was double that obtained in the immobilized batch culture. The productivity of the perfusion run during the growth phase was over ten times that of batch cultures based on reactor volume. Further, this increase also occurred during the non-growth phase. Therefore the production of monoclonal antibodies in a perfusion reactor operated in accordance with the present invention is an efficient alternative to current methods, from the viewpoint of productivity for a given reactor volume.

While this invention has been described with reference to specific embodiments, it is not limited thereto. A wide variety of other embodiments may be devised by those skilled in the art, which embodiments are within the true spirit and scope of this invention, and which are based on the essential teaching hereof. It is intended, therefore, that the appended claims be understood to encompass all such variants and embodiments.

I claim:

1. Method of immobilizing bioactive cells comprising forming a suspension of said cells in a solution of a salt-free osmolarity adjuster which prevents precipitation of alginate in said solution, between 0.25 wt % and 5 wt % alginate and between 10 wt T and 30 wt % polyethylene glycol in water, dividing said suspension into bead-sized globules, between 20 $\mu$ and 5 mm in diameter, contacting said globules with a solution of divalent cations to cause said alginate to gel into gelled alginate beads, and removing said polyethylene glycol from said gelled alginate beads, to produce alginate gel beads of between 20 $\mu$ and 5 mm in diameter containing said cells, said beads containing a multiplicity of enclosed void spaces projecting radially from the center of the beads, and said cells being entrapped in said void spaces.

2. The method of claim 1 wherein said cells are $\frac{1}{2}$ $\mu$ to 30 $\mu$ in diameter.

3. The method of claim 1 wherein said suspension is divided by extrusion of said suspension.

4. A celled alginate bead containing immobilized bioactive cells produced by the method of claim 1.

5. A gelled alginate bead containing immobilized bioactive cells produced by the method of claim 1 wherein said void spaces have a width from 5 $\mu$ to 200 $\mu$, and a length up to the radius of the bead.

6. A gelled alginate bead containing immobilized bioactive cells produced by the method of claim 2 wherein said void spaces have a width from 5 $\mu$ to 200 $\mu$, and a length up to the radius of the bead.

7. The gelled alginate bead containing immobilized bioactive cells of claim 4 or 5 or 6 wherein said bead generally spherical and is between 0.5 mm and 5 mm in diameter.

8. The gelled alginate bead containing immobilized bioactive cells of claim 7 wherein said void spaces have a width from 10 $\mu$ to 200 $\mu$.

9. The gelled alginate bead containing immobilized bioactive cells of claim 4 or 5 or 6 wherein said bioactive cells comprise insect cells.

10. The gelled alginate bead containing immobilized bioactive cells of claim 4 or 5 or 6 wherein said bioactive cells comprise mammalian cells.

11. The gelled alginate bead containing immobilized bioactive cells of claim 4 or 5 or 6 wherein said bioactive cells comprise hybridomas.

12. The gelled alginate bead containing immobilized bioactive cells of claim 4 or 5 or 6 wherein said bioactive cells are anchorage dependent cells and are combined with a compatible anchorage substrate, also included within said void spaces.

13. A method for continuously producing and removing the product of bioactive cells comprising first immobilizing said bioactive cells by forming a suspension of said cells in an aqueous solution of a salt-free osmolarity adjuster which prevents precipitation of alginate in said solution, between 0.25 wt % and 5 wt % alginate and between 10 wt % and 30 wt T polyethylene glycol, dividing said suspension into bead-sized globules of 20 $\mu$ to 5 mm in diameter and contacting said globules with a solution of divalent cations to cause said alginate to form gel beads, removing said polyethylene glycol from said gel beads to produce alginate gel beads of between 20 $\mu$ and 5 mm in diameter containing said cells, said beads containing a multiplicity of enclosed void spaces projecting radially from the center of the beads, and said cells being entrapped in said void spaces and thereafter perfusing a bed of said beads containing said cells with a medium and removing products produced by said cells from the medium.

14. The method of claim 13 wherein said cells are hybridoma ATCC HB 121 cells and said medium is Dulbecco's Modified Eagle Medium.

15. A method as recited in claim 13 wherein said medium also includes cell nutrients for said bioactive cells.

16. A method for obtaining the products of bioactive cells comprising:
mixing said bioactive cells with an aqueous solution of a salt-free osmolarity adjuster which prevents precipitation of alginate in said solution, between 0.25 wt % and 5 wt % alginate and between 10 wt % and 30 wt % polyethylene glycol;
forming porous beads of said mixture by adding bead size globules of said mixture to a divalent ion-containing solution;
removing said polyethylene glycol from said beads to produce alginate gel beads of between 20 $\mu$ and 5 mm in diameter containing said cells, said beads containing a multiplicity of enclosed void spaces projecting radially from the center of the beads, and said cells being entrapped in said void spaces;
placing said beads in a medium including a nutrient for said cells;
allowing said cells to grow and produce cell products in said medium; and
draining at least part of said medium, and separating therefrom cell products.

17. The method of claim 16 wherein said cells are hybridoma ATCC HB 121 cells and said medium is Dulbecco's Modified Eagle Medium.

18. The method of claim 17 wherein said beads are generally spherical and are between 0.5 mm and 5 mm in diameter.

19. The method of claim 16, wherein:
said bead-sized globules are between 0.5 mm and 5 mm in diameter;
said polyethylene glycol has a molecular weight of 8000; and said divalent ion is $Ca^{2+}$.

* * * * *

UNITED STATES PATENT AND TRADEMARK OFFICE
CERTIFICATE OF CORRECTION

PATENT NO. : 5,175,093

DATED : December 29, 1992

INVENTOR(S) : Douglas B. Seifert

It is certified that error appears in the above-identified patent and that said Letters Patent is hereby corrected as shown below:

Column 2, line 54, after "maximum" insert --cell dimensions limited only by the size of the beads to be--.

Column 5, line 19, after "using an", delete "alginate/cell" and insert therefor --alginate/PEG/cell--.

Column 8, line 44, before "be added", delete "ca" and insert therefor --can--.

Column 10, line 66, after "rate of", delete "0.02 hr" and insert therefor --$0.02\ hr^{-1}$.--.

Column 11, Claim 1, line 57, after "10 wt", delete "T" and insert therefor --%--.

Column 12, Claim 4, line 5, after "A", delete "celled" and insert therefor --gelled--.

Column 12, Claim 7, line 16, after "said bead", insert --is--.

UNITED STATES PATENT AND TRADEMARK OFFICE
CERTIFICATE OF CORRECTION

PATENT NO. : 5,175,093

DATED : December 29, 1992

INVENTOR(S) : Douglas B. Seifert

It is certified that error appears in the above-identified patent and that said Letters Patent is hereby corrected as shown below:

Column 12, Claim 13, line 58, after "30 wt", delete "T" and insert --
    %--.

Signed and Sealed this

Thirtieth Day of November, 1993

Attest:

BRUCE LEHMAN

Attesting Officer

Commissioner of Patents and Trademarks